(12) United States Patent
Itoh et al.

(10) Patent No.: US 10,112,077 B2
(45) Date of Patent: Oct. 30, 2018

(54) ELECTRIC TRAINING APPARATUS AND EXERCISE CONTROL METHOD THEREFOR

(71) Applicant: MITSUBISHI ELECTRIC ENGINEERING COMPANY, LIMITED, Tokyo (JP)

(72) Inventors: Haruki Itoh, Tokyo (JP); Masataku Ichikawa, Tokyo (JP); Isao Mizukura, Nagoya (JP)

(73) Assignee: MITSUBISHI ELECTRIC ENGINEERING COMPANY, LIMITED, Tokyo (JP)

( * ) Notice: Subject to any disclaimer, the term of this patent is extended or adjusted under 35 U.S.C. 154(b) by 81 days.

(21) Appl. No.: 15/444,885

(22) Filed: Feb. 28, 2017

(65) Prior Publication Data

US 2017/0274250 A1   Sep. 28, 2017

(30) Foreign Application Priority Data

Mar. 23, 2016   (JP) .................................. 2016-059007

(51) Int. Cl.
*A63B 24/00* (2006.01)
*A63B 22/06* (2006.01)
(Continued)

(52) U.S. Cl.
CPC .......... *A63B 24/0087* (2013.01); *A61B 5/222* (2013.01); *A61B 5/742* (2013.01); *A63B 22/025* (2015.10); *A63B 22/0605* (2013.01); *A63B 71/0622* (2013.01); *A63B 2024/0093* (2013.01); *A63B 2220/30* (2013.01);
(Continued)

(58) Field of Classification Search
CPC . A63B 24/00; A63B 24/0087; A63B 22/0605; A63B 22/025; A63B 71/0622; A63B 5/222; A63B 5/742; A63B 2230/062; A63B 2230/045; A63B 2230/305; A63B 2230/755; A63B 2220/50; A63B 2220/62; A63B 2220/30; A63B 2024/0093
See application file for complete search history.

(56) References Cited

U.S. PATENT DOCUMENTS

5,722,915 A * 3/1998 Reck ................ A63B 21/00178
                                                      482/1
6,261,205 B1 * 7/2001 Elefson ............ A63B 21/00181
                                                      482/135
(Continued)

*Primary Examiner* — Glenn Richman
(74) *Attorney, Agent, or Firm* — Rothwell, Figg, Ernst & Manbeck, P.C.

(57) ABSTRACT

An electric training apparatus is configured to apply, by a load motor, a load on a rotating body configured to apply a load on an exercising person, detect an exercise physiological response value of the exercising person and a number of revolutions of the rotating body, perform control for gradually increasing the load of the load motor toward a set load upper limit value so that a detection result of the exercise physiological response value of the exercising person approaches a target exercise physiological response value set in advance, and change, before an exercise or during the exercise by the exercising person, the load upper limit value in response to a control command input based on a state of the exercising person, a state of the control, and a perceived exertion scale for the exercising person.

19 Claims, 7 Drawing Sheets

(51) Int. Cl.
  *A63B 71/06* (2006.01)
  *A63B 22/02* (2006.01)
  *A61B 5/22* (2006.01)
  *A61B 5/00* (2006.01)

(52) U.S. Cl.
  CPC ....... *A63B 2220/50* (2013.01); *A63B 2220/62* (2013.01); *A63B 2230/045* (2013.01); *A63B 2230/062* (2013.01); *A63B 2230/305* (2013.01); *A63B 2230/755* (2013.01)

(56) References Cited

U.S. PATENT DOCUMENTS

| | | | |
|---|---|---|---|
| 6,805,656 B2 * | 10/2004 | Ogawa | A63B 24/00 482/8 |
| 7,357,209 B2 * | 4/2008 | Kokatsu | B62M 6/45 180/206.2 |
| 2003/0181291 A1 * | 9/2003 | Ogawa | A63B 24/00 482/8 |
| 2003/0186784 A1 * | 10/2003 | Ogawa | A63B 24/00 482/8 |
| 2005/0140113 A1 * | 6/2005 | Kokatsu | B62M 6/45 280/205 |

\* cited by examiner

ELECTRIC TRAINING APPARATUS AND EXERCISE CONTROL METHOD THEREFOR

BACKGROUND OF THE INVENTION

1. Field of the Invention

The present invention relates to an electric training apparatus as typified by exercise therapy apparatus, such as an ergometer and a treadmill, and electric fitness machines, such as an electric fitness bicycle and an electric walking machine, and to an exercise control method for the electric training apparatus.

2. Description of the Related Art

For example, in an exercise therapy apparatus as typified by a related-art ergometer, a pedal rotation speed is detected, and a load torque on the pedals is detected based on a value of a current flowing through a load motor. Further, the load motor is controlled by determining an exercise load based on the obtained detection values of the rotation speed and the load torque.

For example, in Japanese Patent Application Laid-open No. Hei 8-280840, there is disclosed a training apparatus configured to perform, when adjusting an exercise load for an exercising person, load adjustment based on a difference between a detected pulse rate and a target pulse rate within a range equal to or less than an appropriate upper limit load value in order to prevent the detected pulse rate from exceeding the target pulse rate. However, the appropriate upper limit load value can only be set prior to exercise.

Further, in Japanese Patent Application Laid-open No. 2004-113622, there is disclosed an exercise training machine control device including a load adjustment unit that is configured to decrease the load to a minimum level based on vital signals (blood oxygen level, blood pressure, electrocardiographic signal, and pulse sensor) of the exercising person, or based on a load decrease instruction received from outside the device. However, load adjustment cannot be performed based on how "easy" or how "hard" the exercise feels to the exercising person.

SUMMARY OF THE INVENTION

The present invention has been made in order to solve the above-mentioned problems. It is an object of the present invention to provide an electric training apparatus configured to perform load adjustment before an exercise or during the exercise by an exercising person based on a physical condition of the exercising person during the exercise or how "easy" or how "hard" the exercise feels, namely, based on a perceived exertion scale, and to provide an exercise control method for the electric training apparatus.

According to one embodiment of the present invention, there are provided an electric training apparatus and an exercise control method for the electric training apparatus. The electric training apparatus includes: a rotating body configured to apply a load on an exercising person; a load motor configured to apply a load on the rotating body via a transmission mechanism; an exercise physiological response detection unit configured to detect an exercise physiological response value of the exercising person; a number-of-revolutions detection unit configured to detect a number of revolutions of the rotating body; a control unit including an exercise control unit, the exercise control unit being configured to perform control for gradually increasing, based on a detection result from the exercise physiological response detection unit and a detection result from the number-of-revolutions detection unit, the load of the load motor toward a set load upper limit value so that the detection result of the exercise physiological response value of the exercising person approaches a target exercise physiological response value set in advance; a display unit configured to display the detection result from the exercise physiological response detection unit, the detection result from the number-of-revolutions detection unit, and a state of the control of the control unit; and an input unit configured to input a control command to the control unit. The exercise control unit is configured to change the set load upper limit value in response to the control command input from the input unit before an exercise and during the exercise by the exercising person.

According to the present invention, it is possible to provide the electric training apparatus capable of performing load adjustment before an exercise or during the exercise by an exercising person based on a physical condition of the exercising person or a perceived exertion scale, and to provide the exercise control method for the electric training apparatus.

DETAILED DESCRIPTION OF THE PREFERRED EMBODIMENTS

Now, an electric training apparatus according to an embodiment of the present invention is described with reference to the drawings. In the embodiment of the present invention, the same or corresponding portions are denoted by the same reference symbols, and the overlapping description thereof is omitted.

In the following description, there is described, as an example, a case in which an exercising person performs an exercise under the guidance of a doctor or a physical therapist by using, as an example of the electric training apparatus, an ergometer being an exercise therapy apparatus.

First Embodiment

Figure 1:
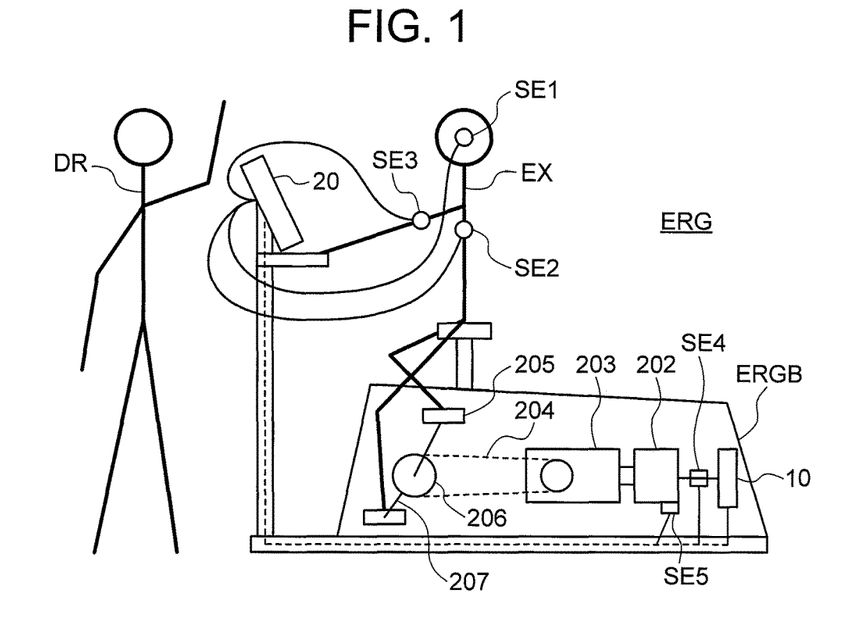
FIG. 1 is a diagram for illustrating a configuration of an ergometer, which is an example of an electric training apparatus according to an embodiment of the present invention.

FIG. 1 is a diagram for illustrating a configuration of the ergometer, which is an example of the electric training apparatus according to the embodiment of the present invention. An exercising person EX sits on a body ERGB of an ergometer ERG to rotate pedals 205. The pedals 205, which are rotating bodies configured to apply a load on the exercising person, are rotatably coupled to a pedal mounting shaft 207. The exercising person may perform an exercise by actually placing his or her feet on the pedals 205. The pedal mounting shaft 207 is mounted to a rotating body 206, which is connected to a transmission mechanism 204 constructed from a belt or the like. A load motor 202, which is configured to apply a load on the pedals 205 via a speed reducer 203, is connected to the transmission mechanism 204. A load torque and the like of the load motor 202 are controlled by a load motor control device 10.

The ergometer ERG includes the following various sensors:

- a pulsometer SE1, which is attached to an ear of the exercising person EX, and is configured to detect a pulse rate;
- a heart rate meter SE2, which is attached to a chest of the exercising person EX, and is configured to detect a heart rate;
- a blood pressure meter SE3, which is attached to an arm of the exercising person EX, and is configured to detect a blood pressure;
- a current sensor SE4, which is arranged between the load motor control device 10 and the load motor 202, and is configured to detect a current flowing through the motor; and
- an encoder SE5, which is a pedaling rate detection unit mounted to the load motor 202 and configured to detect a rotation speed of the motor in order to obtain a pedaling rate of the pedals 205.

Each of those sensors is connected to a control device 20, which includes a touch panel monitor 22 in front of the exercising person EX.

Figure 2:
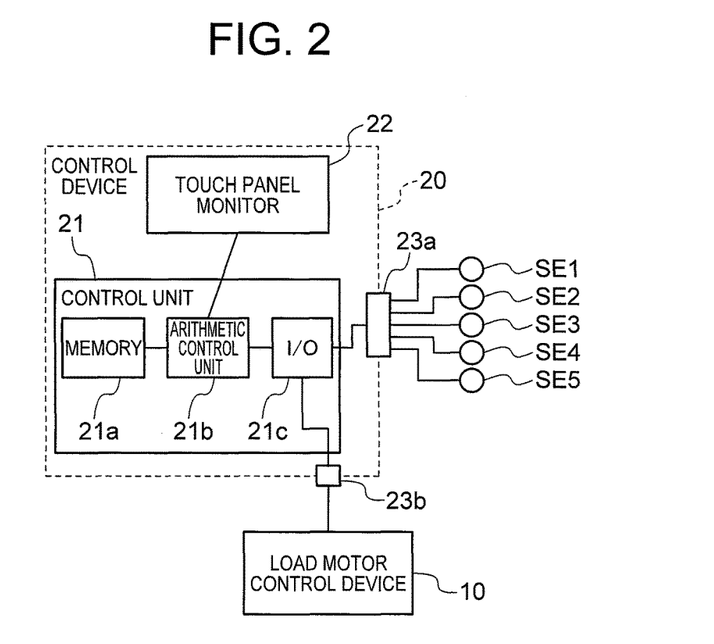
FIG. 2 is a diagram for illustrating an example of a configuration of a control device illustrated in FIG. 1 and peripheral devices thereof.

FIG. 2 is a diagram for illustrating an example of a configuration of the control device 20 and peripheral devices thereof. The control device 20 includes a control unit 21 and the touch panel monitor 22, which is a human interface.

The control unit 21 may be built from a computer. Input and output of external signals are performed by an input/output control unit (I/O) 21*c* via an input interface 23*a* and an output interface 23*b*. Various programs represented by various function blocks illustrated in FIG. 4, FIG. 7, and the like, which are described later, and information, data, processing results, and the like required for the processing are stored in, or stored in advance in, a memory 21*a*. An arithmetic control unit 21*b* including a central processing unit (CPU) is configured to perform arithmetic control based on the various programs, information, and data stored in the memory 21*a* for input signals from the touch panel monitor 22 and external signals input via the input/output control unit (I/O) 21*c*. The arithmetic control unit 21*b* is also configured to output and display processing results on the touch panel monitor 22. Further, the arithmetic control unit 21 b is configured to externally output the processing results via the input/output control unit (I/O) 21*c*, and to store required processing results in the memory 21*a*. A storage unit M described below corresponds to the memory 21*a*.

The control unit 21 of the control device 20 may configure each of the various function blocks, which are described later, by a digital circuit.

Figure 3:
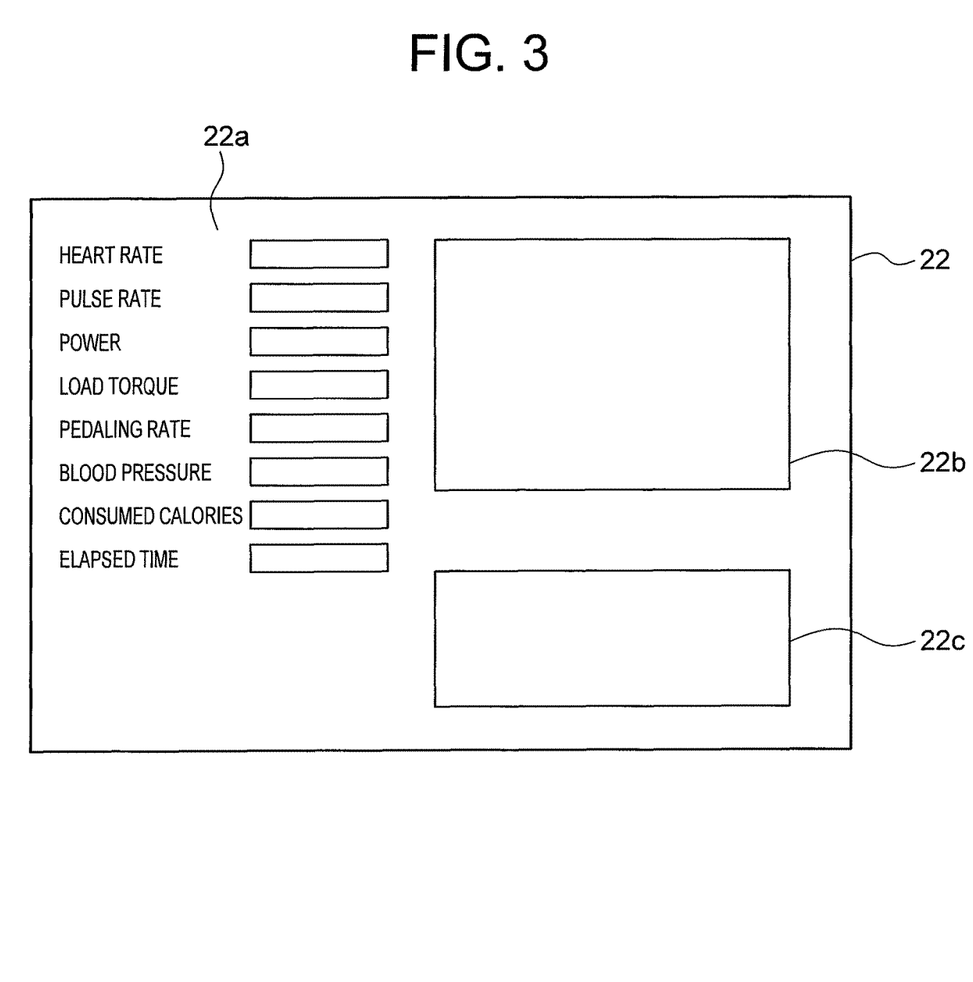
FIG. 3 is a diagram for illustrating an example of a configuration of a touch panel monitor illustrated in FIG. 2.

As in an example illustrated in FIG. 3, the touch panel monitor 22 includes a parameter display area 22*a* configured to display various parameters indicating an exercise state of the exercising person EX, such as "heart rate", "pulse rate", "power (current power)", "load torque", "pedaling rate (number of revolutions per minute)", "blood pressure", "consumed calories", and "elapsed time". The touch panel monitor 22 also includes a free display area 22*b* configured to display changes over time in those parameters in the form of a graph, for example, and an input key area 22*c*. The format of input keys of the input key area 22*c* may be any desired format, such as a format including direction keys and numeric keys, or input keys having a specific input format. The parameter display area 22*a* and the free display area 22*b* form a display unit, and the input key area 22*c* forms an input unit.

Figure 4:
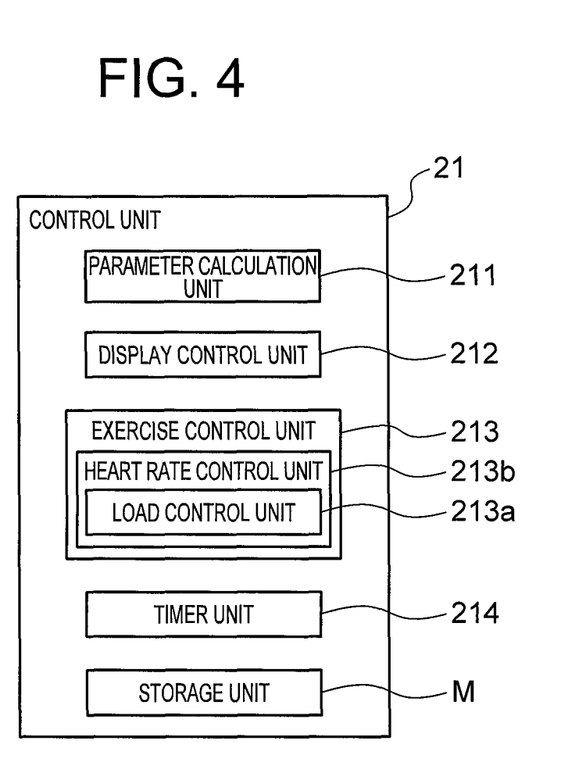
FIG. 4 is a function block diagram of a control unit in the control device illustrated in FIG. 1.

FIG. 4 is a function block diagram of the control unit 21 in the control device 20.

A parameter calculation unit 211 is configured to calculate the above-mentioned various parameters based on input signals.

The "heart rate" is determined based on a signal from the heart rate meter SE2.

The "pulse rate" is determined based on a signal from the pulsometer SE1.

The "power (W)" is determined based on $W = K1 \cdot T \cdot N$.

K1: Constant

T: Load torque generated by the load motor 202

N: Number of revolutions of the load motor 202

The "load torque (T)" is determined based on $T = K2 \cdot Im$.

K2: Constant

Im: Current flowing through the load motor 202 (determined based on the signal from the current sensor SE4)

The "pedaling rate (N)" is determined based on a speed detection signal from the encoder SE5.

The "blood pressure" is determined based on a signal from the blood pressure meter SE3.

The "consumed calories (kcal)" is determined based on $kcal = \Sigma W \cdot K3$ (time integral of W).

K3: Constant

The "elapsed time" is determined based on a timer value in the computer from a timer unit 214.

Further, the determined processing results may be stored in the storage unit M with the elapse of time as necessary.

Note that, the pedaling rate of the pedals 205 is obtained by multiplying the output of the encoder SE5 mounted to the load motor 202 by a transmission gear ratio between the load motor 202 and the rotating body 206. However, for convenience, in the following description, the output of the encoder SE5 is taken as the pedaling rate (N).

A display control unit 212 is configured to display the processing results of the parameter calculation unit 211 and an exercise control unit 213 in the parameter display area 22*a*. Further, for example, time series data of the parameters stored in the storage unit M are displayed as a graph in the free display area 22*b*.

The exercise control unit 213 is configured to control the exercise performed by the exercising person EX based on signals from the various sensors (SE1 to SE5) and a control command input signal from the input key area 22*c*, which is the input unit of the touch panel monitor 22 illustrated in FIG. 3.

The exercise control unit 213 is configured to perform control for gradually increasing the load of the load motor 202 toward a set load upper limit value so that an exercise physiological response value obtained based on the heart rate of the exercising person approaches a target exercise physiological response value. Therefore, it can be seen that a load control unit 213*a* is included in a heart rate control unit 213*b*.

The timer unit 214 is configured to perform time management under the control of the computer in the manner described above, specifically, under the control of the control device 20.

Figure 5:
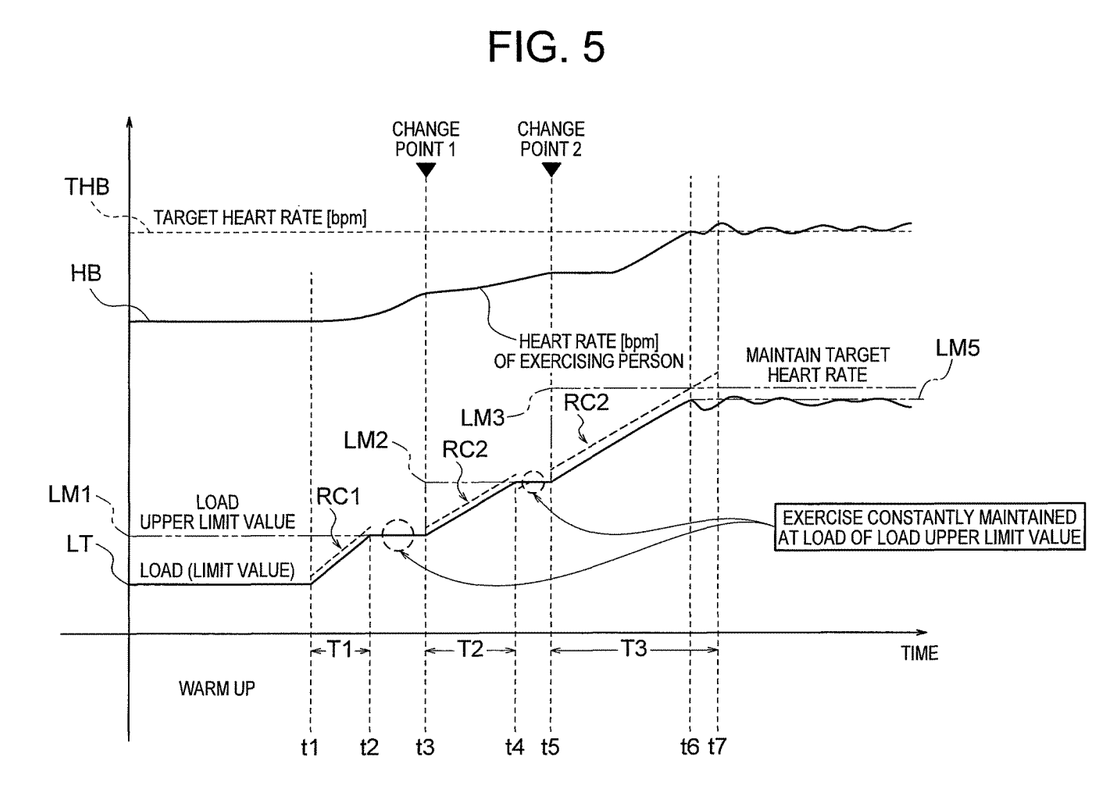
FIG. 5 is a time chart for showing an example of operations under the control of an exercise control unit illustrated in FIG. 4.

FIG. 5 is a time chart for showing an example of operations under the control of the load control unit 213a. When the exercising person EX sits on the erogometer ERG to start an exercise, as an initial setting, a doctor DR, for example, inputs the following parameters from the input unit 22c in consideration of the exercise capacity of the exercising person EX:

- a target heart rate THB;
- a warm-up load LT;
- a first load upper limit value LM1 after the warm up by the exercising person EX; and
- a set period T1 required until the post-warm-up load is increased to the first load upper limit value.

A rate of change RC1 is determined based on those input values.

Further, after those values have been input, the values are stored in the storage unit M as data.

When warming up of a duration set in advance finishes at a time t1, the load of the load motor 202, namely, any one or a plurality of the load torque, the power, and the pedaling rate, is/are increased for the period T1 from the warm-up load to the first load upper limit value LM1. The load LT of the load motor 202 reaches the first load upper limit value LM1 at a time t2, at which the period T1 finishes. After the time t2, the first load upper limit value LM1 is maintained until a time t3, at which a control command to newly change the load upper limit value is input from the input unit 22c, and an exercise is performed at the first load upper limit value LM1. In other words, an exercise with a power at the first load upper limit value LM1 is maintained.

In the present invention, at the time t3, when the doctor DR determines that the load upper limit value is to be increased in consideration of the physical condition and speech or behavior of the exercising person EX, or by referring to, for example, the Borg scale, which is a perceived exertion scale, or the new Borg scale or category-ratio (CR)-10 (RC scale), which is a simplified version of the Borg scale, the doctor DR inputs, for example, a second load upper limit value LM2, which is higher than the first load upper limit value LM1, from the input unit 22c. In this case, the load upper limit value is newly set to the second load upper limit value LM2, and the exercise is continued while further increasing the load.

Note that, the perceived exertion scale is a scale that rates an exercise being performed into levels of perceived exertion, such as "extremely light", "very light", "light", "somewhat hard", "hard", "very hard", and "extremely hard".

Thus, when the load upper limit value is to be changed during an exercise, for example, a rate of change RC2 set in advance, such as that indicated by the dotted line in FIG. 5, is stored in the storage unit M. When the second load upper limit value LM2 is input from the input unit 22c, a period T2 from the time t3 to a time t4 during which the load LT is increased to the second load upper limit value LM2 based on the rate of change RC2 set in advance is set. The load value that is constantly changing based on the rate of change RC2 is a limit value. This point is not shown in detail in FIG. 5 or FIG. 6, but is described later with reference to FIG. 8. Note that, in FIG. 5, RC1 and RC2 only represent the rate of change. In practice, the command values of the rate of changes for the periods T1, T2, and T3 in FIG. 5 coincide with the values indicated by the solid line.

In the exercise having a load upper limit value set as the second load upper limit value LM2, the load LT of the load motor 202 reaches the second load upper limit value LM2 at the time t4, at which the period T2 has elapsed from the time t3. In this case as well, after the time t4, the second load upper limit value LM2 is maintained until a time t5, at which a new control command to change the load upper limit value is input, and the exercise is performed at the second load upper limit value LM2. In other words, an exercise with a power at the second load upper limit value LM2 is maintained.

At the time t5, when the doctor DR similarly determines that the load upper limit value is to be further increased in consideration of the physical condition and speech or behavior of the exercising person EX, or in consideration of the perceived exertion scale, the doctor DR inputs, for example, a third load upper limit value LM3, which is higher than the second load upper limit value LM2, from the input unit 22c. The load upper limit value is newly set to the third load upper limit value LM3 in the same manner, and the exercise is continued while further increasing the load.

In this case, when a heart rate HB [bpm] of the exercising person has reached the target heart rate THB before the load upper limit value LM3 has been reached, at that point, as shown in FIG. 5, the exercising person performs an exercise at a load LM5 at which the heart rate HB [bpm] of the exercising person can be maintained at the target heart rate THB.

The load LM5 is not limited to a constant value. The load LM5 may be constantly increased and decreased repeatedly so that the heart rate HB [bpm] of the exercising person is maintained at the target heart rate THB.

Further, when the heart rate HB [bpm] of the exercising person has reached the target heart rate THB before the initially-set load upper limit value LM1 has been reached, at that point, the exercising person performs an exercise at a load, such as the above-mentioned load LM5, at which the heart rate HB [bpm] of the exercising person can be maintained at the target heart rate THB.

Figure 6:
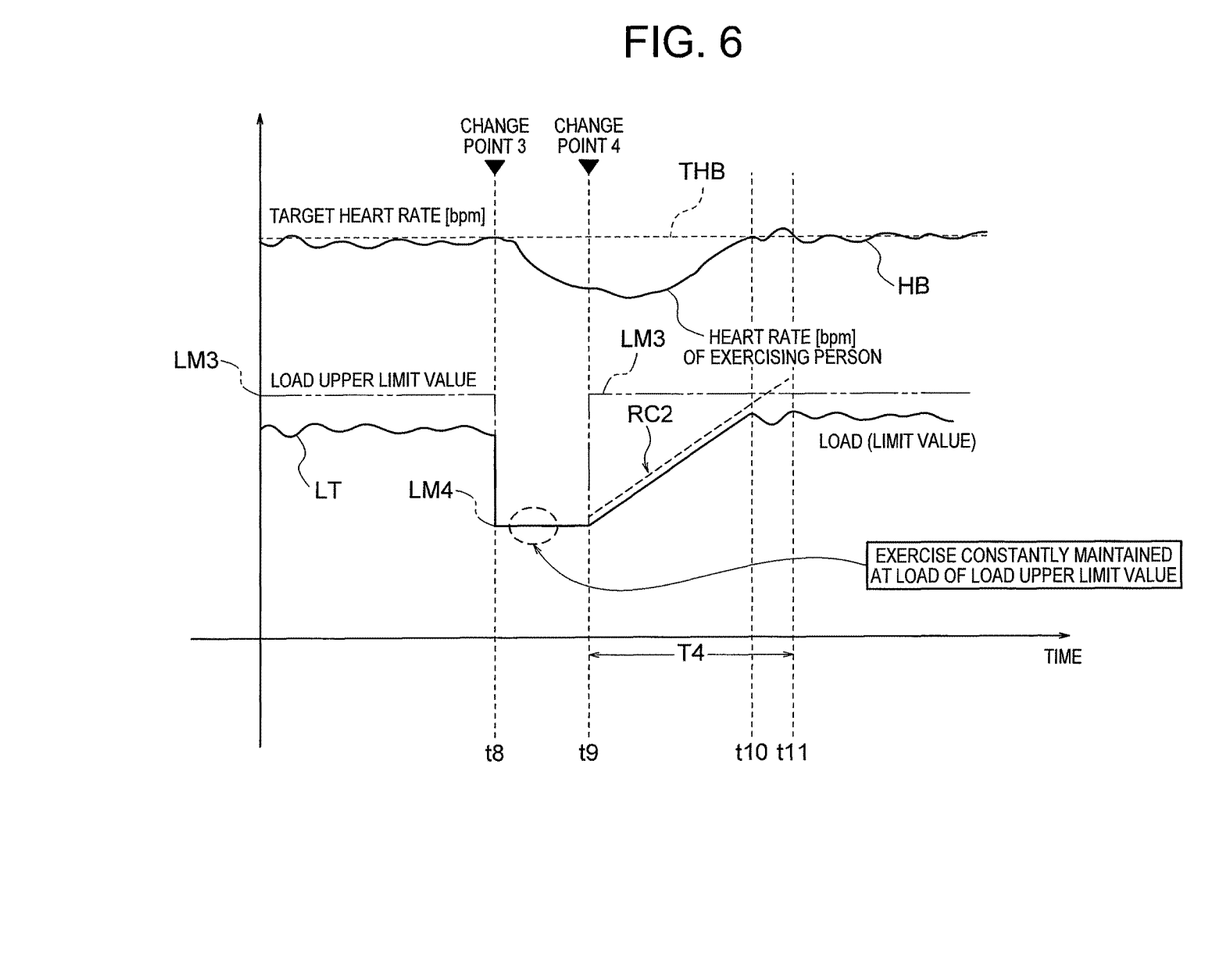
FIG. 6 is a time chart for showing an example of operations under the control of the exercise control unit illustrated in FIG. 4.

FIG. 6 is a time chart for showing an example of operations during the exercise shown in FIG. 5, in which the heart rate HB [bpm] of the exercising person is maintained at the target heart rate THB. When the doctor DR determines, in a state in which the heart rate HB [bpm] of the exercising person is maintained at the target heart rate THB, that it is necessary to temporarily decrease the heart rate HB [bpm] of the exercising person in consideration of the state and speech or behavior of the exercising person EX, or in consideration of the perceived exertion scale, and the doctor DR inputs a fourth load upper limit value LM4 from the input unit 22c at a time t8, the load LT is decreased to the fourth load upper limit value LM4. As a result, the heart rate HB [bpm] of the exercising person is decreased. Further, when there is subsequent input from the input unit 22c at a time t9 for returning the load upper limit value from the fourth load upper limit value LM4 to the third load upper limit value LM3, for example, operation and control similar to the operation and control performed during the period T3 are performed during a period T4 from the time t9 to a time t11, for example.

Note that, when the load LM4 has been input, the load may be instantaneously decreased, as shown in FIG. 6. However, a rate of decrease when decreasing the load may be set in the storage unit M in advance, and the load may be decreased based on that rate of decrease.

Figure 7:
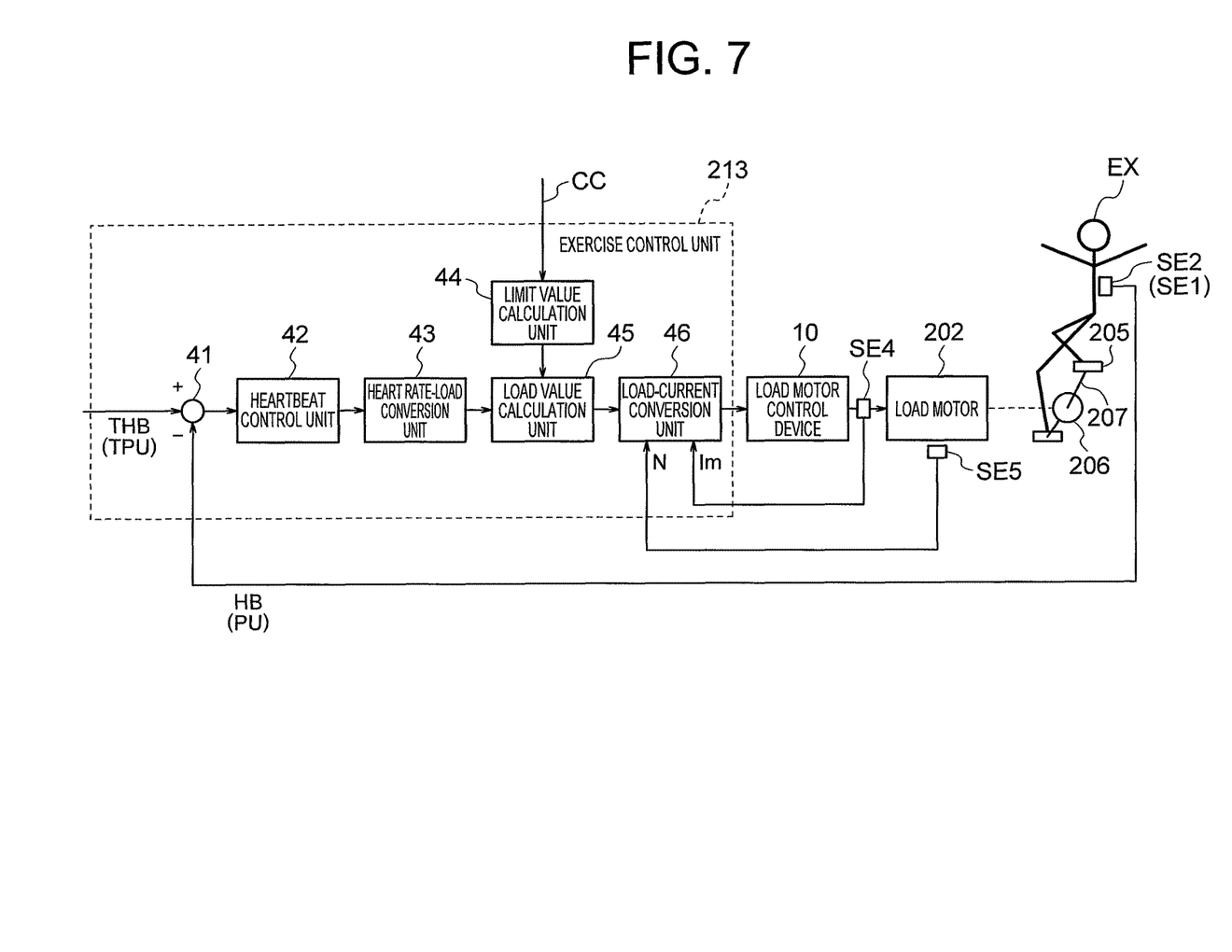
FIG. 7 is a partial configuration diagram for illustrating a flow of operations by the exercise control unit illustrated in FIG. 4.

FIG. 7 is a partial configuration diagram for illustrating a flow of operations by the exercise control unit 213. In FIG. 7, the exercise control unit 213 is illustrated as function blocks.

In the exercise control unit 213, the heart rate control unit 213b, which is an exercise physiological response value control unit, is constructed from a difference calculation unit 41, a heartbeat control unit 42, and a heart rate-load conversion unit 43. The heart rate control unit 213b is configured to perform control so that a detection result of the exercise physiological response of the exercising person EX approaches a target exercise physiological response value set in advance. The load control unit 213a is constructed from a limit value calculation unit 44, a load value calculation unit 45, and a load-current conversion unit 46. The load control unit 213a is configured to perform load control so that a detection result of the exercise physiological response of the exercising person EX approaches a target exercise physiological response value set in advance.

The difference calculation unit 41 is configured to determine a difference between the target heart rate THB stored in advance in the storage unit M and the heart rate HB [bpm] of the exercising person, which is detected by the heart rate meter SE2.

The heartbeat control unit 42 is configured to perform heart rate control for amplifying the difference between the target heart rate THB and the heart rate HB [bpm] of the exercising person.

The heart rate-load conversion unit 43 is configured to convert output of the heart rate control result into a load value.

The limit value calculation unit 44 is configured to calculate a maximum limit value of the load based on the load upper limit value. During the warm-up periods shown in FIG. 5 and FIG. 6 and the periods between the time t2 and the time t3, between the time t4 and the time t5, and between the time t8 and the time t9, during which the load LT has reached the load upper limit value and is constantly maintained at the load upper limit value, the limit value becomes each of the load upper limit values. For other periods during which the load LT is being increased or decreased, the limit value becomes a constantly changing load value in which the load is increased at a constant rate of change up to the set load upper limit value.

For example, during the period between the time t1 and the time t2, the limit value is determined as follows.

Warm-up load+{(first load upper limit value LM1−warm-up load)/(T1)}×(current time−time t1)

Further, when a command CC to change the load upper limit value is input from the input unit 22c, the limit value is determined based on the changed load upper limit value.

The load value calculation unit 45 is configured to select a smaller one of the load conversion value output by the heart rate-load conversion unit 43 and the limit value of the limit value calculation unit 44, and to set the selected value as the load value.

Figure 8:
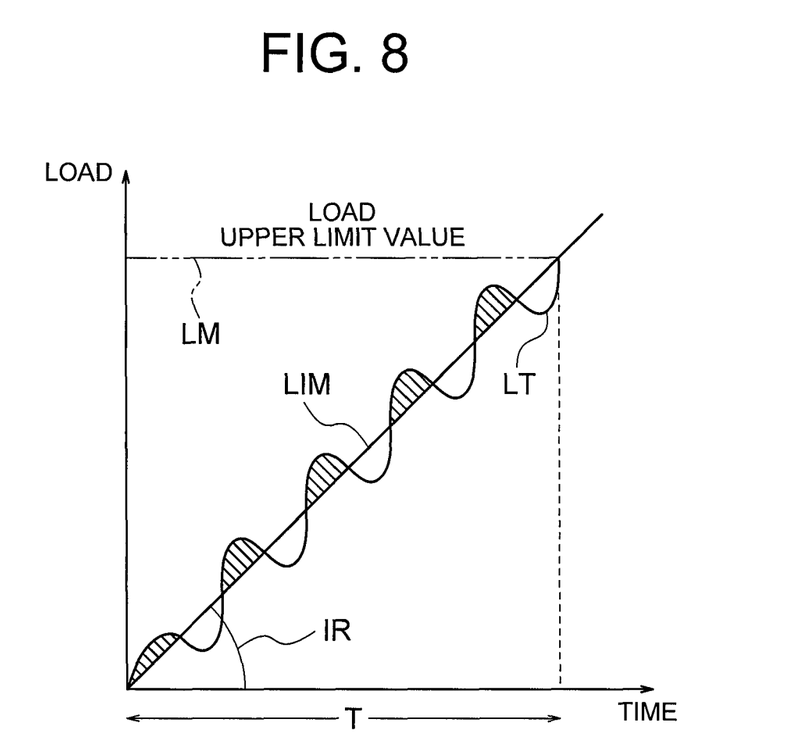
FIG. 8 is a graph for showing a limit value according to the present invention.

In FIG. 8, changes between the load LT increased up to the load upper limit value and a limit value LIM are shown. In FIG. 5 and FIG. 6, the load LT and the limit value LIM are schematically shown together. The limit value LIM linearly increases, for example, based on an increase rate IR (RC1 and RC2 shown in FIG. 5 and FIG. 6) determined based on the load upper limit value LM and a time T to reach. In contrast, the load conversion value of the heart rate-load conversion unit 43 corresponding to the load LT increases in an uneven fashion with respect to the limit value LIM. Because the load value calculation unit 45 is configured to select a smaller one of the load conversion value and the limit value LIM, in the hatched portions in FIG. 8, the limit value LIM is used. As a result, the load LT is prevented from abruptly increasing.

As long as the heart rate HB [bpm] of the exercising person EX does not actually reach the target heart rate THB in the period during which the load is changing, there is no period during which the load LT exceeds the limit value LIM. Therefore, the load LT during the period T becomes the limit value LIM.

The load-current conversion unit 46 is configured to determine the motor current Im based on the following expressions when the load value from the load value calculation unit 45 is W, and a pedaling rate obtained by multiplying the output of the encoder SE5 configured to detect the rotation speed of the load motor 202 by the transmission gear ratio with respect to the number of revolutions of the load motor 202 in the transmission mechanism for the rotating body to which the pedals are mounted is Ns.

W=K1·T·Ns
T=K2·Im
W=K1·(K2·Im)·Ns

The motor current Im may be determined as follows.

Im=W/(K1·K2·Ns)

Controlling the load motor 202 by the load motor control device 10 so that the current of the motor becomes the motor current Im determined by the load control unit 213a enables the load to be increased or decreased so that the heart rate HB [bpm] of the exercising person EX becomes the set target heart rate THB.

In the embodiment described above, the heart rate is used as the exercise physiological response value of the exercising person, but the pulse rate from the pulsometer SE1 may also be used. In this case, a pulse rate PU of the exercising person is used instead of the heart rate HB of the exercising person, and a target pulse rate TPU is used instead of the target heart rate THB. All of the other features may be achieved by replacing the above-mentioned heart rate with the pulse rate. For example, a pulse rate-load conversion unit is used instead of the heart rate-load conversion unit 43.

Further, blood pressure may be used as the exercise physiological response value of the exercising person. In this case, all of the features may be achieved by replacing the above-mentioned heart rate with the blood pressure.

Further, in the above-mentioned embodiment, there is described a case in which an ergometer, which is an exercise therapy apparatus, is used as the electric training apparatus. However, the present invention may also be similarly applied to a treadmill as the exercise therapy apparatus.

In this case, the rotating body configured to apply a load on the exercising person corresponds to the pedals 205 in the ergometer, but to a tread surface in the form of a belt conveyor in the treadmill.

The type of apparatus to which the present invention is applied is not limited to an exercise therapy apparatus to be used in the medical field. The present invention may also be applied to an electric fitness machine, such as an electric walking machine and an electric fitness bicycle, to be used for health management.

Therefore, the present invention may also be applied to electric training apparatus encompassing an electric therapy apparatus and an electric fitness machine.

Further, in the case of an electric fitness machine, when changing the motor load by determining the physical condition of the exercising person, the motor load may be changed not only by a doctor or a physical therapist, but also by an assistant close by the electric fitness machine.

In addition, the exercising person may also change the motor load by determining his or her own physical condition.

In the present invention, the load motor is not specified. Any load motor may be used, such as a direct current (DC) motor, an alternating current (AC) induction motor, a reluctance motor, an AC synchronous motor, a DC synchronous motor, and a linear motor.

Further, in the present invention, as the exercise control unit 213, in FIG. 7, the load-current conversion unit 46 is arranged in the control unit 21, which is provided in the control device. However, the load-current conversion unit 46, the load motor control device 10, and the current sensor SE4 may be arranged in separate devices to serve as a so-called servo motor control device, an inverter, or the like.

In particular, when an assistant who is not a doctor or a physical therapist, or the exercising person himself or herself, changes the motor load by determining the physical condition of the exercising person, for example, the Borg scale or CR-10 (RC scale), which are perceived exertion scales, and a rate of change of the load upper limit value for each level represented in the perceived exertion scale are stored in advance in the storage unit M of the control unit 21 illustrated in FIG. 4. The perceived exertion scale is displayed by the display control unit 212 in, for example, the free display area 22*b* of the touch panel monitor 22 illustrated in FIG. 3. Further, the load control unit 213*a* is configured to change the load upper limit value of the load of the load motor based on the rate of change in accordance with the level of the perceived exertion scale, which is input by the assistant or the exercising person himself or herself based on the displayed perceived exertion scale.

What is claimed is:

1. An electric training apparatus, comprising:
   a rotating body configured to apply a load on an exercising person;
   a load motor configured to apply a load on the rotating body via a transmission mechanism;
   an exercise physiological response detection unit configured to detect an exercise physiological response value of the exercising person;
   a number-of-revolutions detection unit configured to detect a number of revolutions of the rotating body;
   a control unit comprising an exercise control unit, the exercise control unit being configured to perform control for gradually increasing, based on a detection result from the exercise physiological response detection unit and a detection result from the number-of-revolutions detection unit, the load of the load motor toward a set load upper limit value so that the detection result of the exercise physiological response value of the exercising person approaches a target exercise physiological response value set in advance;
   a display unit configured to display the detection result from the exercise physiological response detection unit, the detection result from the number-of-revolutions detection unit, and a state of the control of the control unit; and
   an input unit configured to input a control command to the control unit,
   the exercise control unit being configured to change the set load upper limit value in response to the control command input from the input unit before an exercise and during the exercise by the exercising person.

2. The electric training apparatus according to claim 1, wherein the exercise control unit is configured to maintain, when the load of the load motor has reached the set load upper limit value, the load at the set load upper limit value until a new control command is input.

3. The electric training apparatus according to claim 1, further comprising a storage unit configured to store a perceived exertion scale and a rate of change in the set load upper limit value for each level of the perceived exertion scale,
   wherein the display unit is configured to display the perceived exertion scale, and
   wherein the exercise control unit is configured to change, when a value of a level of the perceived exertion scale is input as the control command from the input unit, the set load upper limit value based on the rate of change stored in the storage unit.

4. The electric training apparatus according to claim 2, further comprising a storage unit configured to store a perceived exertion scale and a rate of change in the set load upper limit value for each level of the perceived exertion scale,
   wherein the display unit is configured to display the perceived exertion scale, and
   wherein the exercise control unit is configured to change, when a value of a level of the perceived exertion scale is input as the control command from the input unit, the set load upper limit value based on the rate of change stored in the storage unit.

5. The electric training apparatus according to claim 1, wherein the electric training apparatus comprises an exercise therapy apparatus comprising one of an ergometer and a treadmill to be used for a medical purpose.

6. The electric training apparatus according to claim 2, wherein the electric training apparatus comprises an exercise therapy apparatus comprising one of an ergometer and a treadmill to be used for a medical purpose.

7. The electric training apparatus according to claim 3, wherein the electric training apparatus comprises an exercise therapy apparatus comprising one of an ergometer and a treadmill to be used for a medical purpose.

8. The electric training apparatus according to claim 4, wherein the electric training apparatus comprises an exercise therapy apparatus comprising one of an ergometer and a treadmill to be used for a medical purpose.

9. The electric training apparatus according to claim 1, wherein the electric training apparatus comprises an electric fitness machine comprising one of an electric fitness bicycle and an electric walking machine for health management.

10. The electric training apparatus according to claim2, wherein the electric training apparatus comprises an electric fitness machine comprising one of an electric fitness bicycle and an electric walking machine for health management.

11. The electric training apparatus according to claim 3, wherein the electric training apparatus comprises an electric fitness machine comprising one of an electric fitness bicycle and an electric walking machine for health management.

12. The electric training apparatus according to claim 4, wherein the electric training apparatus comprises an electric fitness machine comprising one of an electric fitness bicycle and an electric walking machine for health management.

13. The electric training apparatus according to claim 1, wherein the control command is input based on a state of the exercising person, which is displayed on the display unit, the state of the control, which is displayed on the display unit, and the perceived exertion scale for the exercising person.

14. The electric training apparatus according to claims 2, wherein the control command is input based on a state of the exercising person, which is displayed on the display unit, the state of the control, which is displayed on the display unit, and the perceived exertion scale for the exercising person.

15. The electric training apparatus according to claim 3, wherein the control command is input based on a state of the exercising person, which is displayed on the display unit, the state of the control, which is displayed on the display unit, and the perceived exertion scale for the exercising person.

16. The electric training apparatus according to claim 4, wherein the control command is input based on a state of the exercising person, which is displayed on the display unit, the state of the control, which is displayed on the display unit, and the perceived exertion scale for the exercising person.

17. The electric training apparatus according to claim 5, wherein the control command is input based on a state of the exercising person, which is displayed on the display unit, the state of the control, which is displayed on the display unit, and the perceived exertion scale for the exercising person.

18. The electric training apparatus according to claim 9, wherein the control command is input based on a state of the exercising person, which is displayed on the display unit, the state of the control, which is displayed on the display unit, and the perceived exertion scale for the exercising person.

19. An exercise control method for an electric training apparatus, the exercise control method comprising:
applying, by a load motor, a load on a rotating body configured to apply a load on an exercising person;
detecting an exercise physiological response value of the exercising person and a number of revolutions of the rotating body; and
changing, in an electric training apparatus configured to perform control for gradually increasing the load of the load motor toward a set load upper limit value so that a detection result of the exercise physiological response value of the exercising person approaches a target exercise physiological response value set in advance, before an exercise or during the exercise by the exercising person, the set load upper limit value in response to a control command input based on a state of the exercising person, which is displayed on a display unit, a state of the control, which is displayed on the display unit, and a perceived exertion scale for the exercising person.

* * * * *